United States Patent [19]

Ramage

[11] Patent Number: 4,946,971

[45] Date of Patent: Aug. 7, 1990

[54] 6-SULFONYL CHROMANS

[75] Inventor: Robert Ramage, Edinburgh, Scotland

[73] Assignee: Wendstone Chemicals PLC, London, England

[21] Appl. No.: 184,007

[22] Filed: Apr. 20, 1988

[30] Foreign Application Priority Data

Apr. 28, 1987 [GB] United Kingdom ................ 8710065

[51] Int. Cl.⁵ .......................................... C07D 311/70
[52] U.S. Cl. ................................................ 549/408
[58] Field of Search ........................................ 549/408

[56] References Cited

FOREIGN PATENT DOCUMENTS 239354  9/1987  European Pat. Off. .

OTHER PUBLICATIONS

Ramage et al., Tet. Lett., 28(20), 2287–90 (1987).
Paleos et al., J. Org. Chem., 39, 3594 (1974).

Primary Examiner—Nicky Chan
Attorney, Agent, or Firm—Larson and Taylor

[57] ABSTRACT

A class of novel chemical compounds comprising derivatives of 2,2,5,7,8-pentamethylchroman-6-sulphonyl and having the structural formula

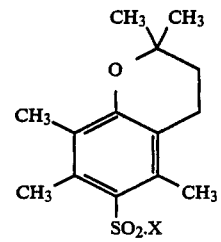

wherein X is selected from halogen and other groups having acidic functionality. We prefer that the X-group be chlorine.

The said compounds are made by the sulphonation of 2,2,5,7,8-pentamethylchroman, preferably using chlorosulphonic acid.

The primary utility of the compounds of the present invention is in the protection of functional groups in organic synthesis and more particularly in the protection of basic functional amino groups, such as amidines and guanidines.

The invention also provides a method of making the protecting group and a protected amino acid.

2 Claims, No Drawings

6-SULFONYL CHROMANS

The present invention relates to chemical compounds, more specifically certain sulphophenyl compounds, their manufacture, their use, particularly as protecting agents in synthesis and the products (and intermediates) so made.

According to the present invention there is provided a class of novel chemical compounds comprising derivatives of 2,2,5,7,8-pentamethylchroman-6-sulphonyl and having the structural formula

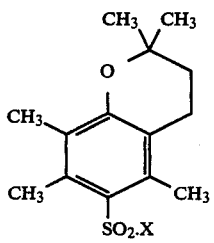

wherein X is selected from halogen and other groups having acidic functionality. Hereinafter, for ease, these chemical compounds will be referred to by the abbreviation "Pmc".

We prefer that the substituent group X should be chlorine.

According to a further aspect of the present invention the said compounds Pmc are made by the sulphonation of 2,2,5,7,8-pentamethylchroman, preferably using chlorosulphonic acid.

The primary utility of the compounds of the present invention is in the protection of functional groups in organic synthesis and more particularly in the protection of basic functional amino groups, such as amidines and guanidines. The protection of amine groups in polypeptide synthesis is well known, but various protecting groups differ in the ease with which they can be attached and the conditions under which they are removed.

Thus, according to yet another aspect of the present invention there is provided a protected amino acid, wherein the protecting group is Pmc.

In general we prefer to use the protecting group Pmc in association with certain dinitrophenyl ethyl compounds (known as Bnpeoc) which are the subject of European Patent Application No. 87302503.5, (published as 0239354) and particularly those Bnpeoc compounds wherein the substituent X is an activated ester.

These compounds have the structural formula

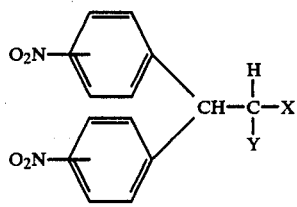

wherein the nitro groups are in the ortho or para positions, X is selected from hydroxyl, halogen and ester groups of aliphatic, aromatic and heterocyclic acids, including esters of substituted acids, and Y is selected from hydrogen and alkyl groups, including substituted alkyl.

Thus the products of the present invention may be used in a manner similar to known protecting groups, such as for example, 4-nitrophenyl ethyl compounds, the 4-methoxy-2,3,6-trimethylbenzenesulphonyl group, or the fluorenyl methoxy carbonyl compound (Fmoc).

However the product Pmc cleaves more rapidly than the 4-nitrophenyl ethyl compounds; it is more readily removed than the 4-methoxy-2,3,6-trimethylbenzenesulphonyl group; and it is more stable and easy to store than the fluorenyl methoxy carbonyl compounds. Thus in general terms, the compounds of the present invention are easier to handle and can be removed more selectively than previously proposed protecting groups.

We believe that the compounds of the present invention are most suited to protect strongly basic amino groups, since the protection can be removed by the use of relatively mild acid treatment, e.g. the use of trifluoroacetic acid (TFA), which does not affect other protecting groups.

The protecting group has been found to be stable in the presence, inter alia, of piperidine, N-ethyl piperidine, N-methyl morpholine, triethylamine, pyridine and sodium hydroxide in methanol, all of which are reagents used in polypeptide synthesis.

As an example of the use of the present invention in the preparation of a protected amino acid, the guanidine side chain of the amino acid arginine can be protected, whilst the amino group can be protected using the succinimidyl derivative of Bnpeoc or Fmoc.

EXAMPLE 1

Preparation of Pmc

The starting material for this synthesis was 2,2,5,7,8-pentamethylchroman and 77.55 g, 0.38 mol was dissolved in trichloromethane (1 liter) and cooled to 0° C. Chlorosulphonic acid (176.85 g, 1.52 mol) in a further 800 ml of solvent was added and the mixture stirred for 15 minutes at 0° C. and then for a further hour without cooling. The reaction mixture was poured onto ice and the organic layer separated off. This organic layer was then washed with 5% sodium carbonate solution, with saturated sodium bicarbonate solution and with brine. The aqueous washings were combined and extracted with more solvent. The original organic layer and the organic extract were combined, dried over anhydrous magnesium sulphate, stirred with activated charcoal and filtered through kieselguhr. Most of the trichloromethane was removed in vacuuo and then petroleum ether (40/60° C.) was added and the remainder of the trichloromethane was removed in vacuo. This crude product was dissolved in more petroleum ether and the solution cooled to 0° C. and filtered to give 45.96 g of Pmc-Cl (yield 39.7%, melting point 77–82° C.).

EXAMPLE 2

Preparation of singly protected arginine

Arginine (L-2-amino-5-guanidino-pentanoic acid) $H_2NC(:NH)NH(CH_2)_3CH(NH_2)COOH$ had its amino acid group protected in known manner with a benzyloxycarbinol group (Z). It was then reacted with the Pmc produced by the method of Example 1 in a reaction mixture containing sodium hydroxide (aqueous) and acetone (72%), the sulpho-chloride moiety reacting with the primary amine group.

EXAMPLE 3

Preparation of protected arginine

The protecting group Z of the product of Example 2 was removed in known manner by hydrogenonolysis over 10% palladium on charcoal. The arginine derivative (now unprotected except as to its side chain) was then dissolved in 5% aqueous sodium carbonate and cooled to 0°. It was then reacted with Bnpeoc-succinimide (equimolar amount) in dimethylformamide. After one hour the reaction mixture was acidified with citric acid and extracted with ethyl acetate. The product was isolated after concentration in vacuuo by precipitation using light petroleum.

EXAMPLE 4

Preparation of protected arginine

In an alternative to Example 3, Fmoc was used in place of Bnpeoc under essentially identical conditions to produce a protected arginine.

EXAMPLE 5

Removal of protecting groups

Removal of the protecting groups Fmoc and Bnpeoc can be effected by the use of a mild base, for example DBN (diazobicyclo(4,3,0)non-5-ene), as more fully described in the said European patent application, without affecting the Pmc group. Similarly the Pmc group can be removed by reaction with trifluoroacetic acid (20 mins. at 20° C., preferably in dichloromethane). Alternatively hydrobromic acid in acetic acid removes the protecting group Pmc in 5 mins. Under the above conditions the protecting groups Bnpeoc and Z are not significantly removed, but the addition of thioanisole to TFA causes some cleavage of the Z group. Removal of the protecting group Pmc as described regenerates 2,2,5,7,8-pentamethylchroman.

EXAMPLE 6

Preparation of polypeptides

Using the above described protected arginine, the following carboxyl terminal-fragments of ubiquitin were prepared using diphenylphosphinic chloride for carboxyl activation:

Z.Arg.(Pmc).Gly.GlyOMe
Z.Leu.Arg(Pmc).Gly.GlyOMe
Z.Arg(pmc).Leu.Arg(Pmc).Gly.GlyOMe
Z.Leu.Arg(Pmc).Leu.Arg(Pmc).Gly.GlyOme In all cases, the products were characterised using suitable analysis techniques as used in the art.

I claim:

1. A compound having the structural formula

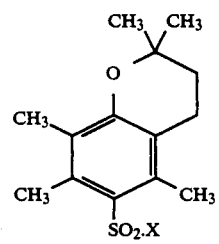

wherein X is halogen.

2. The compound of claim 1, in which the X-group is chlorine.

* * * * *